United States Patent [19]

Goldreyer

[11] 4,365,639

[45] Dec. 28, 1982

[54] CATHETER, CARDIAC PACEMAKER AND METHOD OF PACING

[75] Inventor: Bruce N. Goldreyer, Rancho Palos Verdes, Calif.

[73] Assignee: Applied Cardiac Electrophysiology, San Pedro, Calif.

[21] Appl. No.: 242,705

[22] Filed: Mar. 11, 1981

Related U.S. Application Data

[63] Continuation-in-part of Ser. No. 119,406, Feb. 7, 1980, abandoned.

[51] Int. Cl.³ .............................................. A61O 1/04
[52] U.S. Cl. .............................. 128/786; 128/419 PG
[58] Field of Search ........... 128/41 AO, 41 P, 41 PG, 128/784, 785, 786

[56] References Cited

U.S. PATENT DOCUMENTS

| | | | |
|---|---|---|---|
| 3,345,990 | 10/1967 | Berkovits | 128/419 PG |
| 3,769,998 | 11/1973 | Muench | 128/419 P |
| 3,804,084 | 4/1974 | Friedman | 128/786 |
| 3,825,015 | 7/1974 | Berkovits | 128/419 P |
| 3,903,897 | 9/1975 | Woolons et al. | 128/419 P |
| 3,915,174 | 10/1975 | Preston | 128/786 |
| 3,937,226 | 2/1976 | Funke | 128/419 D |
| 3,977,411 | 8/1976 | Hughes, Jr. et al. | 128/786 |
| 4,060,090 | 12/1977 | Lin et al. | 128/419 PG |
| 4,154,247 | 5/1979 | Ongill | 128/419 P |

Primary Examiner—William E. Kamm
Attorney, Agent, or Firm—Fulwider, Patton, Rieber, Lee & Utecht

[57] ABSTRACT

A cardiac pacemaker with a single catheter for insertion into a heart through the vascular system. An electrode system for the catheter including a stimulating electrode at the distal end of the catheter for positioning at the apex of the right ventricle, with the stimulating electrode connected to the pulse generating unit of the pacemaker, and sensing electrodes on the catheter spaced from the stimulating electrode for positioning adjacent to the wall of the right atrium for sensing signals generated by the atrial excitation or P-wave, with the P-wave signals connected as input to the pacemaker for determining the timing of the ventricular stimulating pulses.

The sensing electrodes are circumferentially equidistant from the stimulating electrode and provide one or more bipolar signals for the pulse generating unit.

In alternative configurations, the stimulating electrode and the sensing electrodes are positioned in various locations within the heart to provide other methods of cardiac control.

42 Claims, 25 Drawing Figures

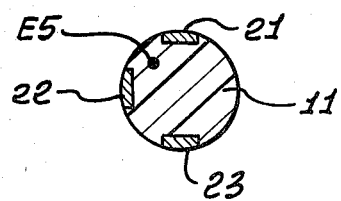
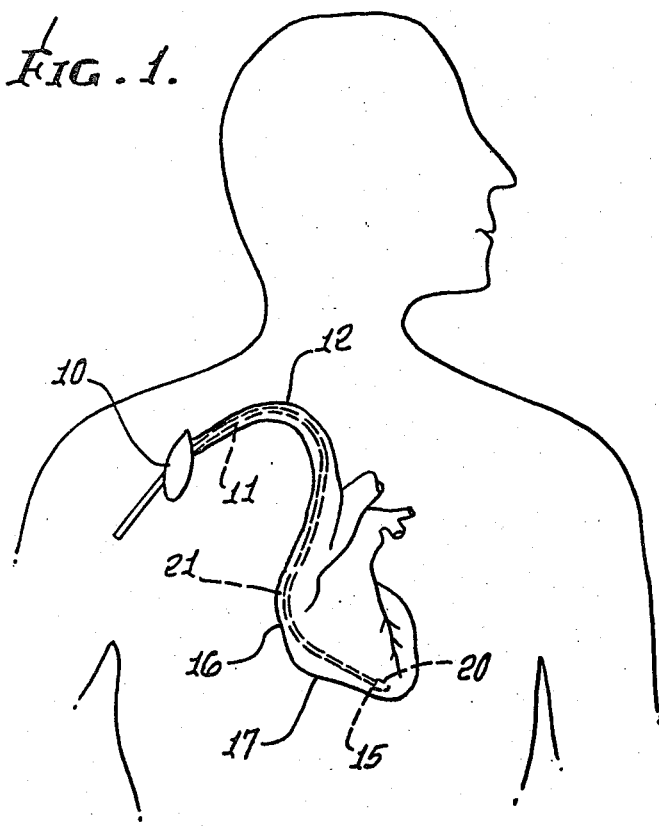
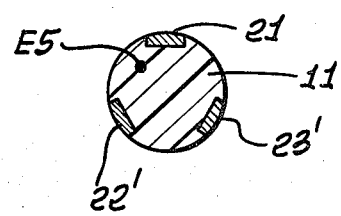
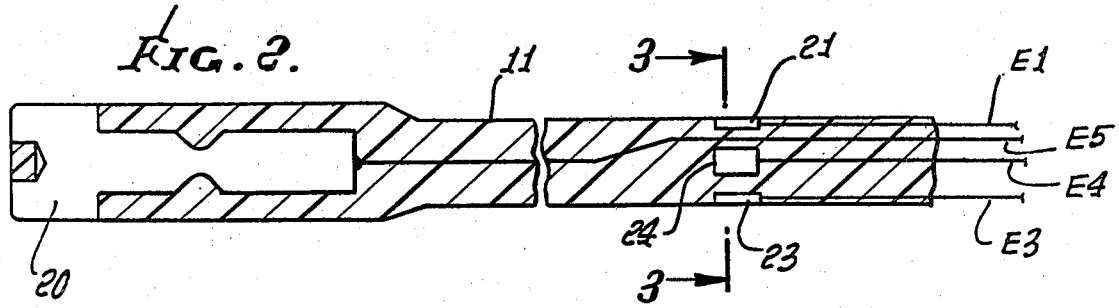
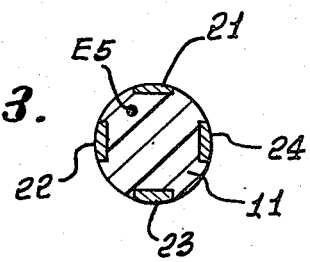
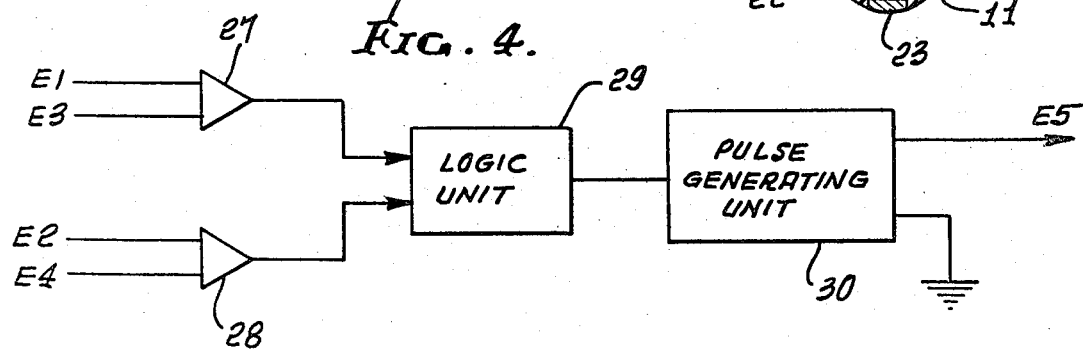

CATHETER, CARDIAC PACEMAKER AND METHOD OF PACING

CROSS-REFERENCE TO RELATED APPLICATION

This application is a continuation-in-part of copending application Ser. No. 119,406, filed Feb. 7, 1980, now abandoned.

BACKGROUND OF THE INVENTION

This invention relates to cardiac pacemakers and in particular, to a new and improved electrode system for a pacemaker.

Cardiac pacemakers are widely used for stimulating the heart and controlling its rate. The heart has an internal electrical system. Electrical signals produced by the sino-atrial (SA) node control the heart beat under normal circumstances. These signals conduct from the SA node to the right atrium, and are transmitted through the heart to the right ventricle which responds to the transmitted signal producing contraction of the heart. Malfunction in the conduction system between atrium and ventricle sometimes results in failure of signal transmission. Cardiac pacemakers supply this missing signal to the ventricle and result in its beating at a fixed rate.

In a typical cardiac pacemaker, the electrical pulses are provided at a predetermined rate. In earlier versions, the electrode was sewn into the right ventricle requiring open heart surgery. Through later developments, the electrode was mounted in a catheter which was inserted through a vein permitting positioning of the electrode at the apex of the right ventricle, and thus eliminating the requirement for open heart surgery. With this type of pacemaker, the atrium is depolarized at physiologic body rate determined by signals from the SA node, while the ventricle operates at the predetermined rate controlled by the pacemaker. This is not a wholly satisfactory condition, particularly for active people who require a heart rate varying over a wide range, or for people with severely limiting heart disease.

In one approach to meeting this problem, two catheters were utilized, with one catheter positioned within the ventricle and one within the atrium. The stimulating electrodes of the two catheters are operated at a fixed rate but with a time lag between the stimulating pulses. This system, sometimes referred to as sequential pacing, is not widely used and can augment cardiac output by only 5-15%.

In a more recent system, the P-wave generated at the atrium is sensed by an electrode sewn into the atrium at the time of open heart surgery. The signal from the sensing electrode is connected to the pulse generator and controls the timing of the stimulating pulse applied to the electrode of the catheter positioned in the ventricle. This system provides for varying the heart rate as a function of body demand, but has not been satisfactory because of the open heart surgery required for implanting the sensing electrode in the atrium.

Other electrode configurations for cardiac catheters are shown in U.S. Pat. Nos. 3,825,015, 3,865,118, 3,903,897 and 4,154,247. In 3,825,105, two axially spaced ring electrodes are placed at the distal end and four more axially spaced ring electrodes are carried on the catheter spaced from the distal end so as to be located in the atrium. Both ventricle and atrium are stimulated and the two atrial electrodes providing best contact with the atrium are selected for use.

U.S. Pat. No. 3,865,118 discloses a system for sequential pacing. Two stimulating electrodes are provided in the atrium and two in the ventricle. Stimulating pulses are sent in sequence to the atrium and to the ventricle. An alternative form of synchronized pacing possibly useful on a short-term basis is discussed at column 7 lines 10-20. The patent states that the atrial electrode could act as a sensor of the patient's T waves, apparently as well as acting as a stimulating electrode, since the preceding sentence refers to atrial stimulating being an advantage. At column 8 lines 1-5, the patent indicates that more or less than two electrodes could be used, but no details of construction or use are given.

In U.S. Pat. No. 3,903,897, two axially spaced ring electrodes are placed at the distal end and two more axially spaced ring electrodes are carried on the catheter spaced from the distal end so as to be located in the atrium. Both pairs of electrodes are used for sensing, with the ventricle signal being used for a discrimination function. The ventricle electrodes are also used for stimulation. Although theoretically practical, extensive literature indicates that P waves thus sensed are generally of small amplitude and more significantly that discrimination of P waves from QRS complexes is virtually impossible. The performance of a ring electrode sensor is shown in FIG. 16, which will be described below.

U.S. Pat. No. 4,154,247 discloses a catheter having two stimulating electrodes for improved stimulation. In most disclosed embodiments one stimulating electrode is at the distal tip and the other is a ring spaced from the tip. The catheter is formed so that the ring makes direct contact with the tissue of the heart. In one embodiment, the catheter is branched with a stimulating ring electrode in each branch so that both electrodes can make contact.

It is an object of the present invention to provide a new and improved electrode system which will provide for varying the heart rate in response to the body demand while at the same time utilizing only a single catheter inserted through a vein, without calling for open heart surgery. A particular object of the invention is to provide a new and improved sensing electrode arrangement which produces one or more usable P-wave signals, or in one embodiment QRS signals, for stimulation and timing.

It is an object of the invention to provide a catheter for sensing and for stimulation in the form of a single nondiverging filament having a stimulating electrode at the distal tip and having two or more sensing electrodes closely adjacent each other and circumferentially mounted in the catheter equidistant from the tip.

It is another object to provide a new and improved signal handling circuit and process for generating and utilizing orthogonally related P type signals in achieving an improved P wave signal for use in a cardiac pacer, which signals may be manipulated in operational amplifiers and the like if desired.

It is a particular object of the invention to provide new and improved processes for controlling heart action using a sensed bipolar signal or orthogonal bipolar signals as inputs for controlling or inhibiting pace maker action. Another object is to provide new and improved electrode-heart configurations for stimulation of heart action. Other objects, advantages, features and results will more fully appear in the course of the following description.

SUMMARY OF THE INVENTION

The electrode system of the present invention utilizes a single catheter for insertion into the heart through the vascular system, with the electronics for the cardiac pacemaker being mounted subcutaneously on the anterior chest wall and connected to the electrodes by conductors in the catheter. In one embodiment stimulating electrode means, typically a single electrode, is mounted at the distal end of the catheter for positioning in the apex of a right ventricle. The catheter enters the heart through the cephalic vein and passes through heart valves to the right ventricle. Sensing electrode means, typically one or two pairs of opposed circumferentially mounted electrodes, are carried on the catheter and spaced proximally from the stimulating electrode means, for positioning adjacent to the wall of the atrium. The catheter is in the form of a single nondiverging filament. The sensing electrodes preferably are connected in pairs for producing bipolar signals, with each signal varying as a function of the cardiac P wave. It has been found that the cardiac P wave can be sensed by electrode means of this circumferential design positioned adjacent to the atrial wall; it is not required that a sensing electrode be embedded in the muscle. Differential amplifier circuitry provides for sensing P wave voltages and discriminating against QRS complexes, which because of the sensing electrode configuration are of miniscule amplitude when compared to sensed P waves, and combining orthogonal P wave voltages to obtain an extremely high level P wave signal.

An important feature of the invention is the unique catheter configuration of separate sensing and stimulation electrodes, all in a single filament, with the sensing electrodes close to each other and equidistant from the catheter tip, and with the sensing electrode portion of the catheter free floating in the heart, which provides for bipolar sensing of heart action separate from stimulation, and discrimination against stimulation pulses and undesired heart action signals.

In alternative embodiments, the locations of the stimulation electrode and the sensing electrodes are varied to provide VVI pacing with QRS sensing and AAI operation for intermittent sinus node dysfunction.

BRIEF DESCRIPTION OF THE DRAWINGS

FIG. 1 is a diagrammatic illustration of a portion of a human body illustrating the installation of the cardiac pacer of the present invention;

FIG. 2 is an enlarged sectional view of the catheter of FIG. 1 showing the electrode system;

FIG. 3 is a sectional view taken along the line 3—3 of FIG. 2;

FIG. 4 is an electrical block diagram illustrating a preferred configuration for the electronics of the pacer;

FIGS. 10 and 11 are sectional views similar to that of FIG. 3, showing alternative embodiments of electrode positions;

DESCRIPTION OF THE PREFERRED EMBODIMENTS

Figure 5:
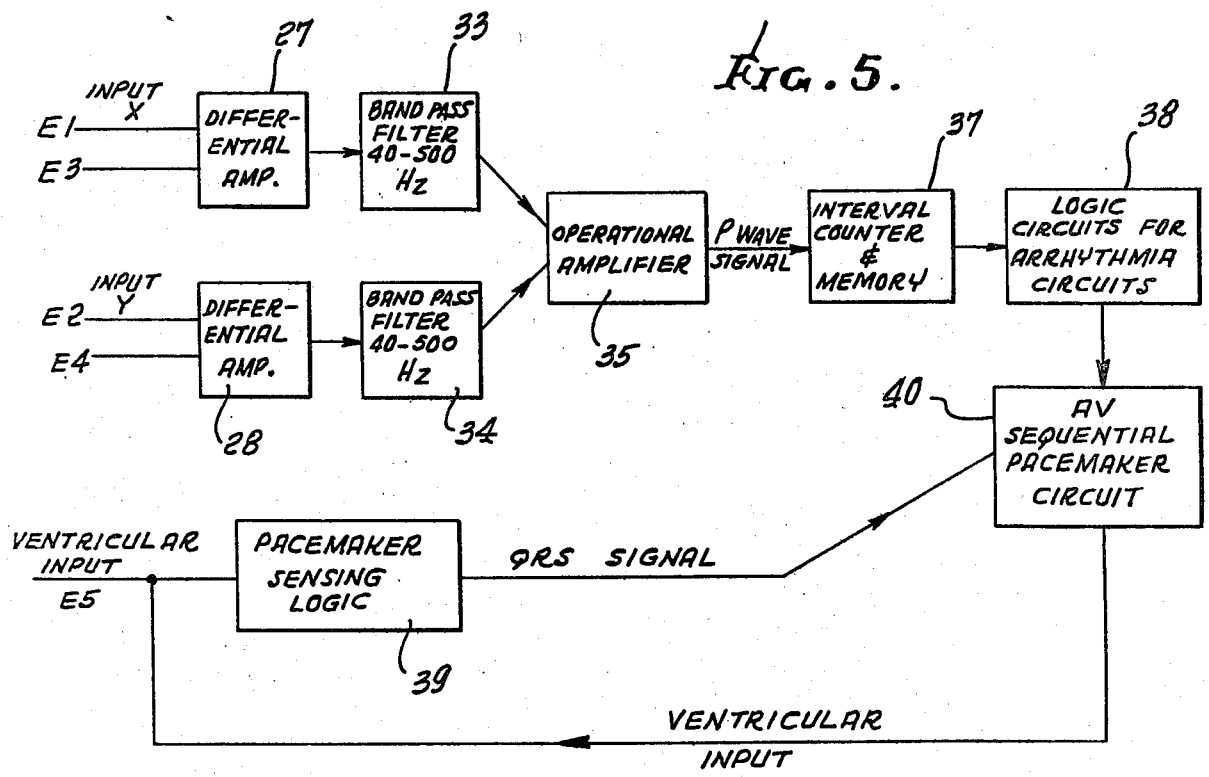
FIG. 5 is an electrical block diagram showing the electronics in greater detail and incorporating the presently preferred embodiment of the invention.

FIG. 1 illustrates a cardiac pacemaker as installed in a human body. An electronics package 10 is inserted under the skin at the upper right of the chest and a catheter 11 is inserted in the cephalic vein 12. The catheter is secured to the vein in the conventional manner for maintaining the catheter in the inserted position. The distal end 15 of the catheter is inserted into the heart through the right atrium 16 to the apex of the right ventricle 17. This is the conventional location for the distal end of the catheter of a cardiac pacer. The catheter is in the form of a single nondiverging filament.

A stimulating electrode 20 is mounted at the distal end of the catheter 11 and is connected to the electronics package 10 by a conductor E5 within the catheter. A variety of electrode configurations have been utilized for the stimulating electrode and any of those are suitable for the present invention. A unipolar system is illustrated in FIG. 2 utilizing a single stimulating electrode 10. In an alternative configuration, a bipolar system could be used, with two spaced electrodes at the distal end of the catheter.

Atrial sensing electrodes are carried in the catheter spaced a short distance (typically 10–16 cm) from the stimulating electrode 20. In the embodiment illustrated, four electrodes 21, 22, 23, 24 are provided. The sensing electrodes are spaced from the distal end of the catheter a distance so that when the catheter is inserted with the distal end in the apex of the ventricle, the sensing electrodes are positioned adjacent the wall of the right atrium, preferably adjacent the high lateral wall, as shown in FIG. 1. However the essentially linear nature of the catheter tends to prevent the electrodes from making direct contact with the heart tissue. It is desirable to have the electrodes freefloating within the heart chamber as this prevents endocardial fibrosis of the electrodes, which would tend to cause attenuation of the sensed signal. The sensing electrodes 21–24 are connected to the electronics package 10 by conductors E1–E4, respectively, in the catheter.

The sensing electrodes sense the cardiac P wave in the atrium and produce signals representative of the P wave. In the preferred configuration, at least one pair of electrodes is utilized to provide a bipolar signal. In the embodiment illustrated, electrodes 21, 23 are connected as inputs to a differential amplifier 27 and electrodes 22, 24 are connected as inputs to another differential amplifier 28. The electrode set 21, 23 provides a bipolar signal which varies as a function of a component of the P wave. The electrode set 22, 24 provides another bipolar signal which varies as a function of another component of the P wave, orthogonal to the first component.

The outputs of the differential amplifiers 27, 28 are connected as inputs to a logic unit 29 which functions to select the larger of the amplifier output signals to use as an input to a pulse generating unit 30. The pulse generating unit 30 may be conventional in design and provides the stimulating pulse on conductor E5, with the other output connected to the body adjacent the electronics package to serve as the circuit ground. The amplifiers 27, 28, the logic unit 29 and the pulse generating unit 30 are contained in the electronics package 10.

By way of example, the logic unit 29 could include a voltmeter circuit connected to each incoming differentially amplified atrial signal. The analog signal from each amplifier 27, 28 would then be represented as a digital figure of discrete voltage—e.g. 21-23=4.3 mv. and 22-24=0.7 mv. The logic unit would consider a P wave to have been accurately detected if either incoming signal has a voltage >1 mv. Although the 0.7 mv. signal is marginal and might be considered possible "false" sensing of a P wave, the 4.3 mv. signal would meet the logical criteria indicating detection of a P wave and this information would then be fed to a pulse generator of standard P synchronous design. The logic unit would select the larger of the two signals if both exceeded the 1 mv. limit.

Figure 24:
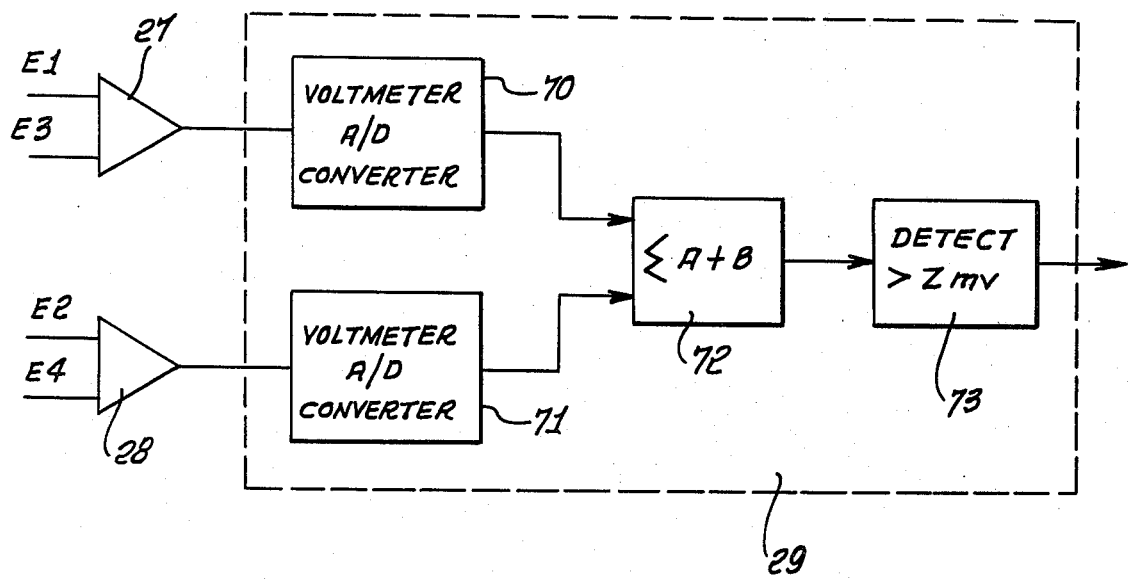
FIGS. 24 and 25 are electrical block diagrams similar to that of FIGS. 4 and 5 showing additional circuit details of alternative embodiments.

Alternatively, electrically combining or summing the atrial signals derived from electrodes 21-23 and 22-24 might be a more sensitive and discriminatory way of obtaining more accurate P wave sensing, and a summing circuit is shown in FIG. 24. In FIG. 24, the logic unit 29 includes voltmeter and analog to digital converters 70, 71, a summer 72, and a level detector 73. Each peak to peak analog atrial signal is electronically measured and assigned a digital (numerical) value without sign in converters 70, 71. The two digital figures are then numerically added in summer 72 yielding a specific number—in the example provided, 4.3+0.7=5.0 mv. The detector 73 is programmed to "detect" a P wave if the combined voltage then exceeds 2 mv. Logic circuitry as described above is well known in the art.

In studies performed in more than 30 patients atrial electrogram voltages averaged 2.47±1.7 mv. The addition of voltages derived from two orthogonally oriented electrode pairs would be virtually certain of exceeding 2 mv. On the other hand, QRS voltages measured via these same orthogonal atrial electrodes averaged 0.07 mv. and in 28 electrogram signals no QRS voltage was detectable at all. Thus, the combined QRS voltage would virtually never exceed the 2 mv. "detect" specification and thus only real P waves would be detected as P waves by the logic circuit.

This electrode configuration provides for delivering the stimulating pulse to the desired location in the ventricle and also provides for sensing the P wave in the atrium to provide control for the pulse generating unit, without requiring open heart surgery or electrode insertion in a muscle, and requiring only a single catheter. By positioning the distal end of the catheter at the apex of the ventricle and affixing the catheter to the vein, the sensing electrode configuration is maintained in position adjacent the atrium wall, providing a stable orientation and a relatively strong signal from the atrium. At the same time, good rejection of the R wave is achieved. While two sets of sensing electrodes for producing two bipolar signals are illustrated, the system may be operated with one set of electrodes for providing one bipolar signal. Alternatively three electrodes may be used to provide two bipolar signals, with one electrode common to both signals. The use of three electrodes is illustrated in FIGS. 10 and 11, with the electrodes spaced at 90° in FIG. 10 and at 120° in FIG. 11. In FIG. 10, electrodes 21 and 22 may form a first pair to provide a bipolar signal on conductors E1 and E3, and electrodes 23 and 22 may form a second pair to provide a bipolar signal on conductors E2 and E4, with E3 and E4 connected together, either within the catheter or outside as desired. Similar electrode connections may be made in FIG. 11.

The catheter typically is in the order of two to four millimeters in diameter and in the order of 60 centimeters in length between the electronics package and the distal end. For atrial sensing and ventricle stimulating, the sensing electrodes typically are in the order of 10 to 18 centimeters from the distal end, this spacing being determined by the size of the heart. The electrodes are radially spaced from each other about the periphery of the catheter at the same distance from the distal end. This configuration permits sensing a strong P wave, with little interference.

Figure 6:
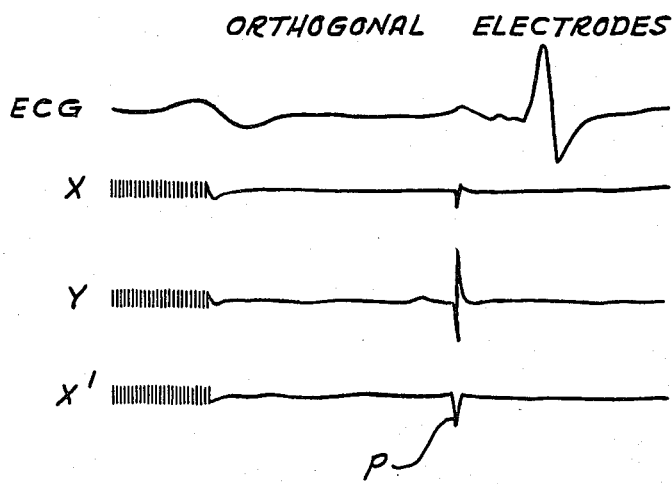
FIG. 6 is a copy of an electrogram illustrating P wave signals achieved by the sensing electrode means of the present invention.
Figure 16:
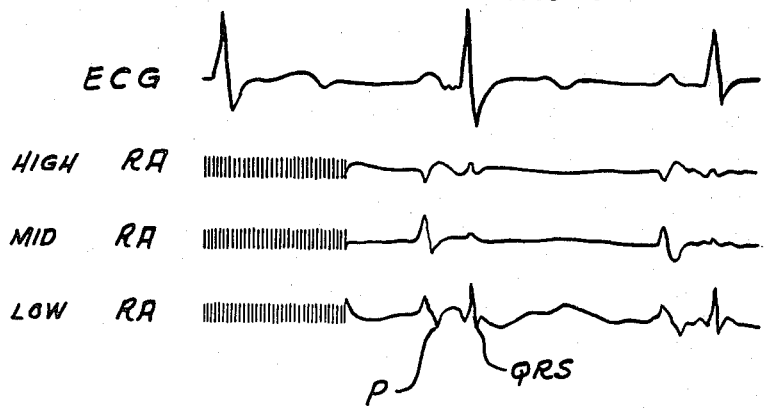
FIGS. 16–22 are copies of electrograms similar to that of FIG. 6 illustrating various heart signals.

Two electrograms taken on the same patient, one after the other, are shown in FIGS. 6 and 16. In both electrograms, the upper trace is a conventional ECG indicating the voltage measured at the skin. The high frequency signal at the left in the three lower traces of each electrogram is a calibration signal with an amplitude of 1 millivolt.

The electrogram of FIG. 16 was made utilizing a catheter with three pairs of ring electrodes of the type shown in the aforesaid U.S. Pat. No. 3,903,897. One pair was located in the high right atrium, one pair in the mid-right atrium, and one pair in the low right atrium. The ECG trace shows a typical heart action as measured by the voltage at the skin of the patient. In each of the atrium signals, the P wave precedes the QRS complex with the amplitude of the P wave approximately the same as the amplitude of the QRS complex.

The electrogram of FIG. 6 was produced by substituting the catheter of the present invention for the ring electrode catheter in the measuring system. This catheter utilized three electrodes, corresponding to electrodes 21, 22 and 23 of FIG. 3. The x trace is the signal measured between electrodes 21 and 22, the y trace is the signal measured between electrodes 22 and 23, and the $x^1$ trace is the signal measured between electrodes 21 and 23. The P wave signal shows clearly on each on the three traces. However, there is no signal at the time of QRS complex, indicating that the new electrode configuration sharply discriminates against the QRS complex when operating in the atrium.

Since the catheter is not affixed to the wall of the atrium, movement of the catheter by respiration or changing arm positions or physical activity might move one or more electrodes into a new position relative to the atrial wall. An important advantage of the use of two bipolar signals is that having orthogonal sensing capabilities, even if the x component of the P wave were to be diminished, the y would probably increase. As a result the overall amplitude of the signal would not vary as much with electrode motion. In studies on 27 patients the positioning of the sensing electrode in the higher lateral atrium resulted in P wave signals which ranged from ½ to 7 millivolts in the x or y direction and when electronically summed generally resulted in 5 to 7 millivolt P wave signals. The QRS complex signals ranged from zero to one-half millivolt, with all but two less than one quarter millivolt.

Figure 17:
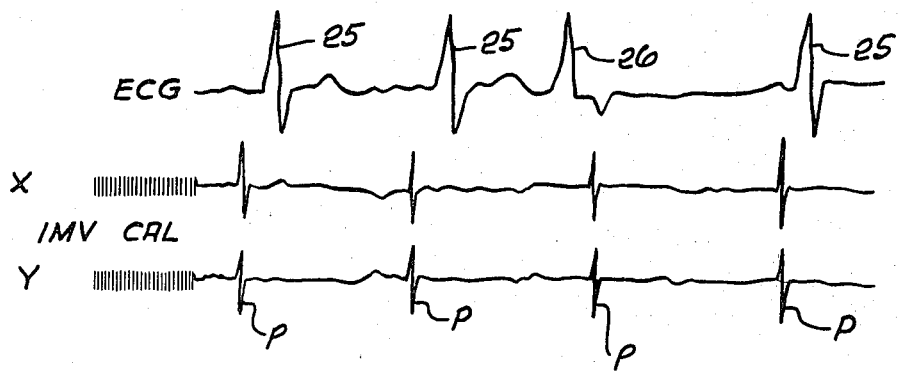

QRS complexes whether normally conducted or the result of ventricular ectopic activity or ventricular pacing are essential undetectable at the atrial level. FIG. 17 is an electrogram similar to that of FIG. 6, with normal QRS signals at 25 and a QRS signal due to premature ventricular contraction (PVC) at 26. The x and y P wave signals are substantial, while there is little or no QRS signal picked up by the orthogonal electrodes in the atrium. This is because the two to four sensing poles of this catheter are so equally distant from the ventricular myocardium that the differential amplifier used to process the signals sees no difference between the ventricular depolarization seen at electrodes 21, 22, 23 or 24. Hence, virtually no signal is recorded at all. Even unipolar ventricular pacing and pacing spikes are discriminated against with this electrode catheter sensing configuration.

Figure 18:
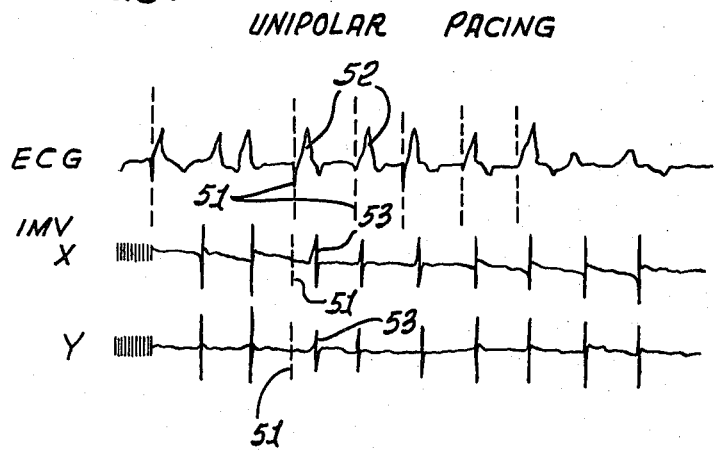
Figure 19:
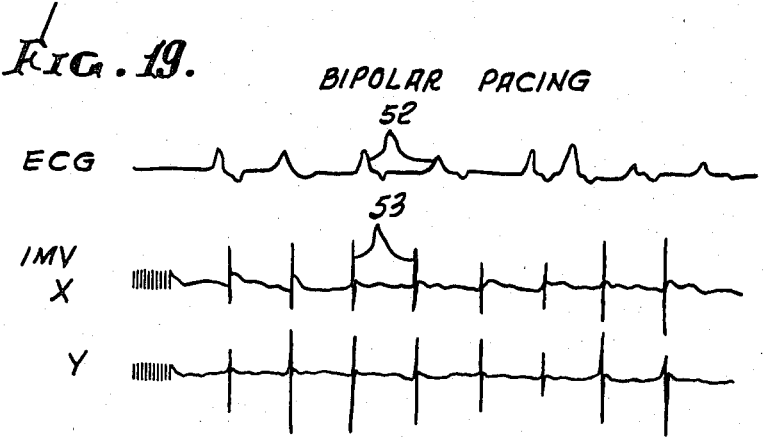

This is illustrated in FIGS. 18 and 19 which are electrograms obtained in the same manner as that of FIG. 6. During this measurement, the heart was being paced independent of the signals received by the sensing portion of the catheter. In the unipolar pacing, one stimulating electrode was positioned in the ventricle and the other beneath the skin; in the bipolar pacing, both stimulating electrodes were positioned in the ventricle. In the ECG wave, the pacing pulses or stimulus are shown at 51 and the QRS complexes at 52. In the unipolar pacing, a small pacing pulse appears on the x and y traces of lesser magnitude than the P wave signals 53, but the QRS complex signals are substantially non-existent. In the bipolar pacing, the pacing pulses 51 are not measured by the ECG since both electrodes are within the heart. Also, the pacing pulses do not appear on the x and y traces.

As an alternative to selecting the larger of the two bipolar signals from the two pairs of electrodes, the two signals may be processed in various ways to provide an output of greater magnitude and yet representative of only the P wave. By way of example, where the signals from the two electrode pairs are designated x and y respectively, (1) x and y can be utilized in an orthogonal relation producing a vector loop, with the area of the ellipse or loop providing the output, (2) an operational amplifier can take the integral of x plotted against y, developing a numerical value to represent the P wave, (3) the first derivative of the rate of rise of x and y can be multiplied to generate a value which represents the P wave, (4) the total deflection of x and y (in absolute millivolts) can be added or multiplied to develop a number reflective of the P wave, (5) a loop representing a plot of x vs. y can be generated and its circumference used as a numerical value to indicate the P wave.

A circuit showing a cardiac pacer for alternative (1) is set out in greater detail in FIG. 5.

Conductors E1, E3 from a pair of opposed electrodes provide input x to differential amplifier 27. Conductors E2, E4 from the other pair of opposed electrodes provide input y to differential amplifier 28. The voltage pulses at inputs x and y are shown in FIG. 6. The initial large and rapid deflection corresponds to the P wave of the electrocardiagram and has been measured in the range of 1 to 6 millivolts. The subsequent small and sometimes notchy deflections following the initial large and rapid deflection correspond to the QRS complex.

Figure 7:
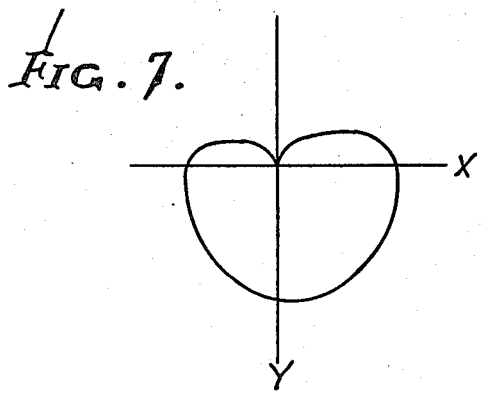
FIGS. 7–9 are diagrams illustrating the operation of the system of the invention.

The outputs of the differential amplifiers are passed through band pass filters 33, 34, respectively, typically having a pass band in the range of 40 to 500 hertz. The filtered outputs are connected to an operational amplifier 35 which may be conventional and which provides a descrete P wave loop as shown in FIG. 7. Alternatively, the operational amplifier may determine the area within the loop resulting from the plot of x versus y.

Figure 8:
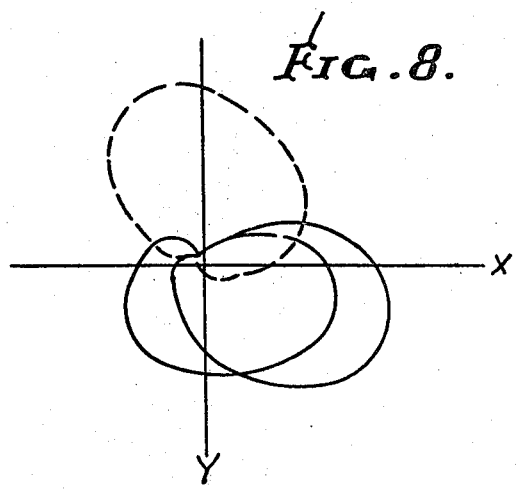

With this type of sensing system, the amplitude of x may vary with respect to that of y and the directions x and y may shift with shifts in position of the catheter within the right atrial chamber. The orientation of the loop may vary in amplitude and direction with such shifts, but the total area would remain substantially constant. See for example, FIG. 8 showing three such loops where the area under the curve of a loop irrespective of sequence or direction of atrial depolarization indicates P wave activity which cannot be confused with ventricular activity. Ventricular activity appears only as a minor deflection within the central area of the loop. Hence the signal representing the area within the loop, determined either by analog or digital means, is an accurate measure of the P wave which is readily discriminated from the QRS complex.

The remainder of the circuit includes an interval counter and memory 37, logic circuits for arrhythmia analysis 38, conventional pacer sensing logic 39, and conventional AV sequential pacer circuit 40. The pacer relies on both sensing of atrial depolarizations and sensing of ventricular responses.

Figure 9:
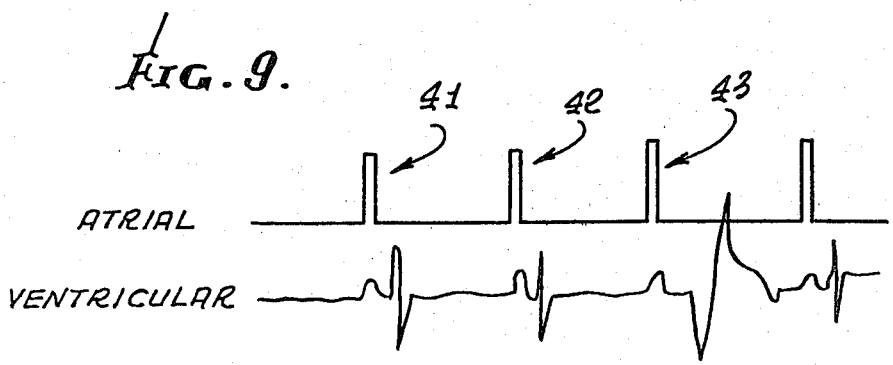

With the patient in normal sinus rhythm, as each atrial wave is sensed a digital signal is sent from the operational amplifier 35 to the pacer circuit 40 to state that a P wave has been sensed. Once a P wave has been sensed the pacer circuit would then wait 140 to 200 milliseconds (depending upon the way it is programmed) and if no ventricular depolarization is sensed by the ventricular portion of the electrode catheter, an impulse sufficient to stimulate the ventricle would be generated and delivered. See FIG. 9, where two normally conducted P waves 41, 42 with a normal PR interval are followed by a failure of AV conductions 43. Under this circumstance the pacer would fire in the demand mode with a preset PR interval of approximately 200 milliseconds.

The operational amplifier 35 sends out a specific signal of known characteristics which represents the P wave. This signal is fed to interval counter 37 which compares the P to P interval of the sensed beat with the stored interval of the average of the ten prior P wave intervals sensed. The interval counter may be combined with logic circuits 38 for arrhythmia analysis with the capability of discriminating atrial premature beats, flutter, fibrillation and paroxysmal atrial tachycardia from appropriate increases in sinus rate. The output from the logic circuits is fed to the AV sequential pacer circuits 40, which may include programmable parameters such as high and low rate limits, PR interval, pulse duration, and pulse amplitude.

The input from conductor E5 connected to the electrode at the distal end of the catheter, i.e., the ventricular input, is processed by ordinary pacer sensing logic 39 and QRS signal developed, which is fed into the AV sequential pacer circuit 40 and, when appropriate a ventricular output or stimulating pulse is fed to the ventricle.

The analog atrial electrogram signals derived from the electrode pairs 21-23 and 22-24 may be considered the X and Y input to an operational amplifier which takes the "electrical" area under the loop described by X vs. Y. The amplifier would be a standard operational amplifier which integrates X as a function of Y deriving a digital value. A specific digital value exceeding preset limits would represent "detection" of a P wave and would then activate the P synchronous pacing output circuitry.

Varying the pulse rate of the signal at E5 as a function of a sensed electrical signal is a well known technology using equipment currently available from commercial sources, including the Cordis Corporation. The circuit design is best shown in U.S. Pat. No. to Thaler 4,091,817, wherein a P wave control, R wave inhibited ventricular stimulation device is described; and is also shown in U.S. Pat. No. to Lin, et al., 4,060,090 wherein the PR interval decreases as a function of the rate of the detected P waves. Both of these types of circuits could be used in the pulse generator of the present invention including item 30 in FIG. 4 and item 40 in FIG. 5. P wave synchronous technology is well known and further details are given in Nathan, et al. Am. J. Cardiol. 11:362-7, 1963; and Kruse, et al., Pace 3:641, 1980.

Figure 25:
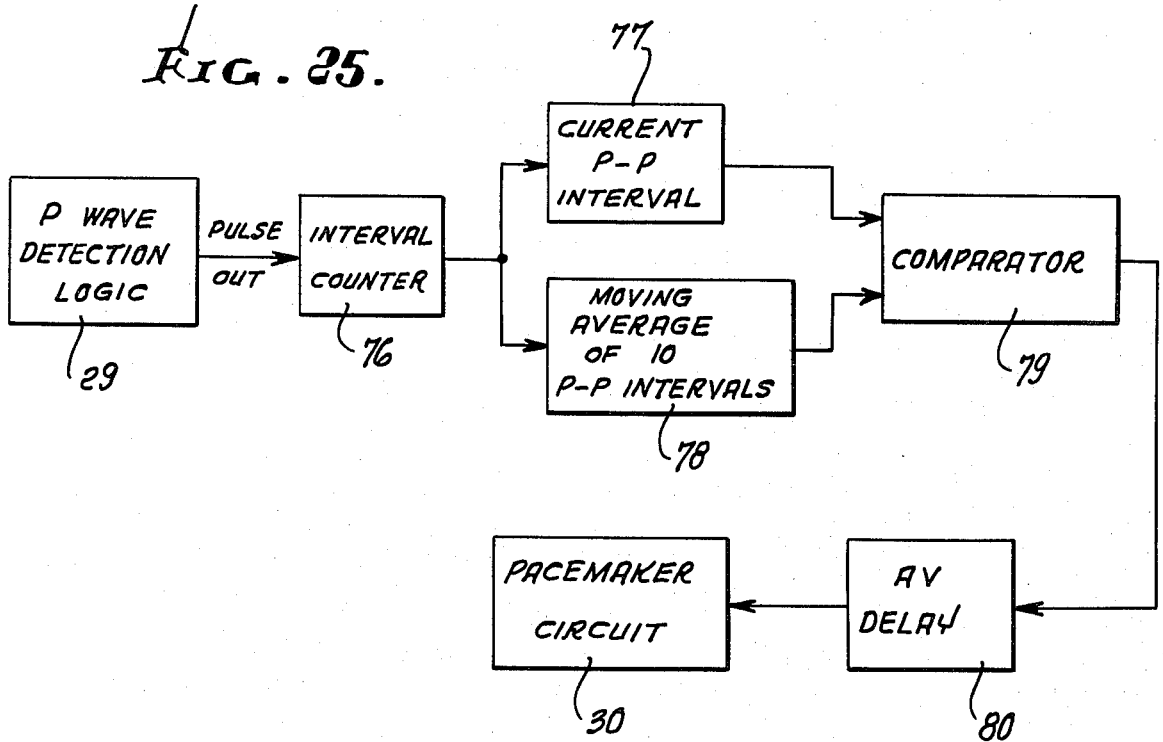

The deviation of occurrence of a P wave signal from prior P wave signals may be detected and used to initiate a pacing pulse, when such deviation is outside predetermined limits. A circuit for performing this function is shown in FIG. 25, including an interval counter 76 and a comparator 79 for comparing the current P wave to P wave interval (P-P) from a register 77 and the average of ten P-P intervals from an averaging unit 78. The comparator output is connected to a conventional AV delay unit, which in turn is connected to the stimulating pulse generating unit 30 (or 40).

Once a P wave is detected by whatever means, the output of the detection logic 29 will go to the interval counter 76 which will determine each successive P-P interval in msec. This digital information will be computed into a moving average of the 10 previous P-P intervals using standard digital circuitry 78. The current P-P interval from 77 will be compared (digitally) to the current average P-P interval from 78. If there is a <10% difference, normal sinus rhythm will be logically assumed, and the currently sensed atrial signal (P wave) will enter a circuit 80 with a variable AV delay and from there to the ventricular stimulating circuits 30.

If the current P-P interval is curtailed by 30-40% of the averaged P-P intervals, a ventricular stimulating pulse will be generated but with a longer AV delay programmed to vary inversely with the extent of the curtailed cycle. If the current P-P is curtailed by 74%, no ventricular output will be generated.

In operation, the cardiac pacer provides a stimulating pulse to the heart at a rate which varies to match the rate called for by the body, while at the same time utilizing only a single catheter which is readily inserted and maintained in position. A signal which varies as a function of the P wave is produced by the sensing electrode structure adjacent the atrium wall. The catheter may at times lie against the wall, but will usually lie adjacent and in close proximity to the wall. Physical contact between electrodes and atrial myocardium is not required and would probably be detrimental due to progressive fibrosis and signal attenuation. This electrode system senses and provides a strong P wave signal without sensing QRS complexes and provides such a signal for use with the conventional AV pacer circuit.

Figure 12:
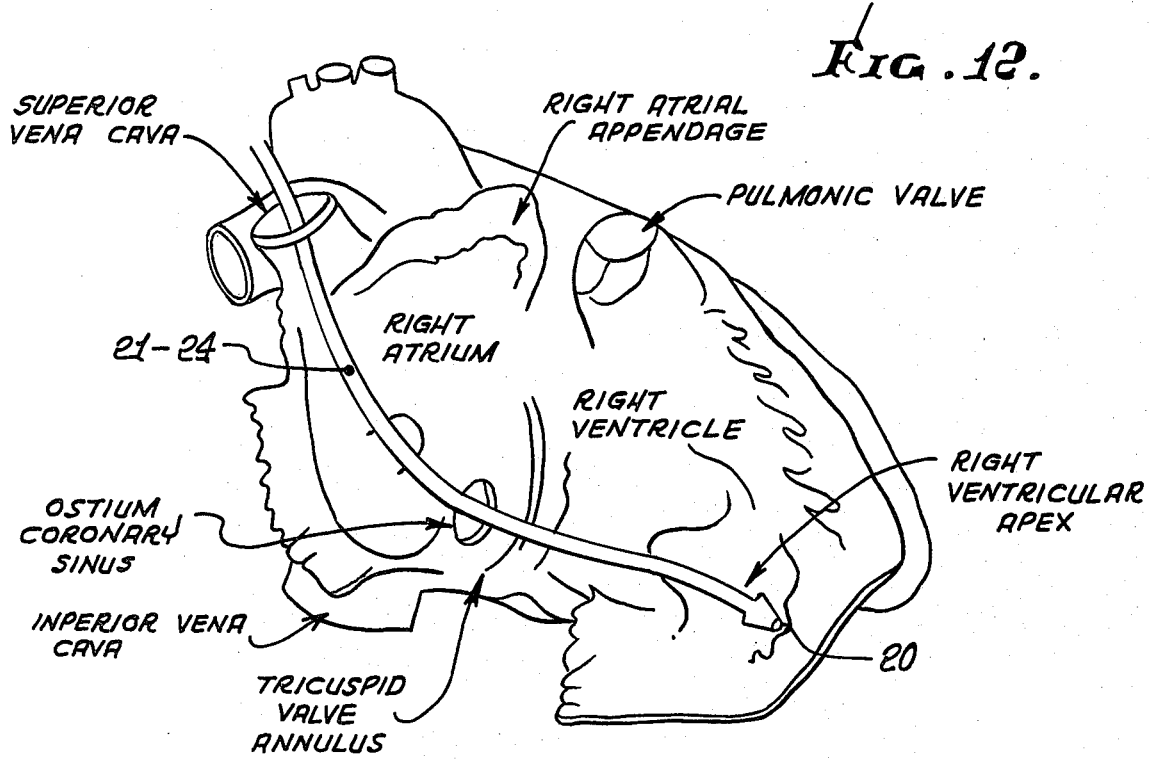
FIG. 12 is an enlarged view of a heart illustrating the presently preferred positioning of the catheter of the invention.

The position of the catheter of the invention for atrial sensing and ventricle stimulation is shown in greater detail in FIG. 12, wherein various components of the heart are labeled.

Figure 13:
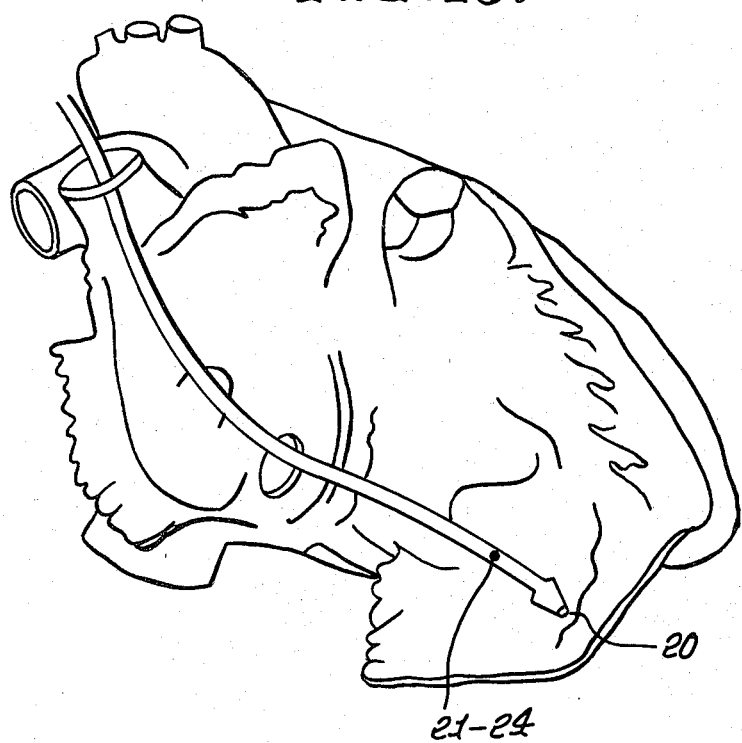
FIGS. 13, 14 and 15 are views similar to that of FIG. 12 showing alternative positionings of the catheter.

An alternative positioning of the catheter for use in ventricle sensing and ventricle stimulation is shown in FIG. 13, with the sensing electrodes 21-24 in the ventricle near the stimulation electrode. This type of operation is generally designated as VVI type pacing. In ordinary electrode catheter configurations with unipolar stimulating catheters, a unipolar signal derived from the ventricle and the anode located under the chest wall is used for sensing and stimulating. In bipolar systems, the two ring electrodes at the ventricular level are used for both sensing and placing. There have been considerable problems with sensing in the ventricle using either of these systems. In the unipolar system, muscle tremor artifact and electronic noise from the external environment may be seen by the catheter and sensed as QRS complexes. With a bipolar system although external signals are less well sensed it is not infrequent that other components of the ventricular repolarization such as T waves are seen, or that ventricular premature depolarizations are not seen by this type of catheter system.

Using a bipolar sensing device in the ventricle which does not participate in ventricular stimulation, would allow all ventricular events to be sensed, and normally the signal from the QRS would be so strong that virtually no outside electrical interference, P wave, or T wave sensing would be likely using the catheter of the present invention.

In prior art VVI methods and apparatus, sensing and stimulation has been performed with the same electrode or electrodes. With this arrangement, the sensing system sees the stimulation pulse and the stimulation artifact, but not the QRS complex and hence cannot really indicate whether or not there has been any heart response to the delivered electrical stimulus.

The positioning of FIG. 13 is for a pacing system which utilizes ventricular sensing and ventricular pacing—a standard VVI mode of ventricular pacing wherein as long as the patient remains with a heart rate above the set rate of the pacemaker there is no stimulation. Signals are sensed on electrodes located one or a few centimeters back from the pacing tip and two, three, or four such free floating circumferential electrodes are used to sense the QRS complex. If no QRS complex is sensed within the specified period of time, standard pacemaker logic is utilized to stimulate the right ventricle through the distal electrode.

Figure 20:
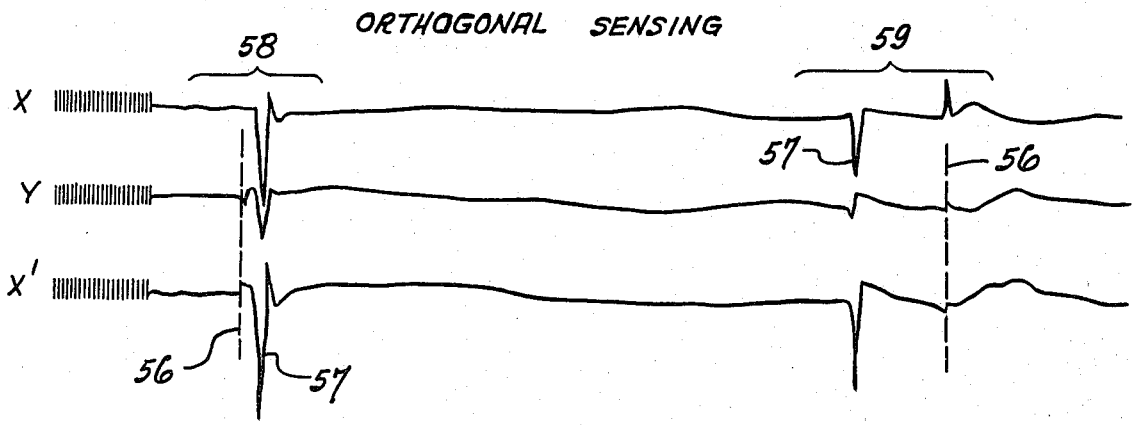

There are certain theoretic advantages to using a sensing system which is independent of the pacing distal electrode. For example, one can judge by looking at the electrogram recorded from the proximal yet still ventricular site whether or not the stimulus delivered at the distal electrode resulted in a ventricular response. This is illustrated in the electrogram of FIG. 20. The catheter used for producing this electrogram had a pacing electrode at the tip to provide the stimulus pulse, and three sensing electrodes positioned about the catheter equidistant from the tip at a distance such that the electrodes were in the ventricle, as shown in FIG. 13. The sharp spike 56 is the stimulus pulse produced by the unipolar pacer, and the more complex pulse 57 is the sensed heart action, namely the QRS complex. Referring to the pulses at 58, the heart action is produced by the stimulus and occurs within 15 to 20 milliseconds. The electrogram shows that the electrode configuration of the invention will sense this heart action. The pulse group 59 at the right of FIG. 20 shows heart action occurring prior to the stimulus, with the stimulus producing no heart action because it occurs during the refractory period, that is, the period after heart action when another heart action can not be generated. Heretofore because of polarization changes at the tip electrode, the evoked QRS was obscured by the stimulus artifact. With orthogonally spaced electrodes at the ventricular level, the stimulus artifact appears as a very discrete spike 56 and the QRS is a large amplitude three to five millivolt signal 57 clearly distinguishable from the stimulus artifact.

Figure 22:
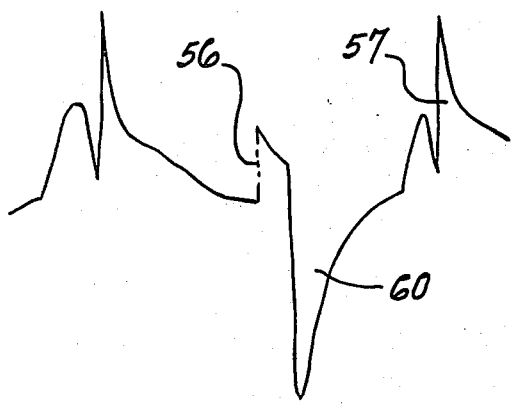
Figure 21:
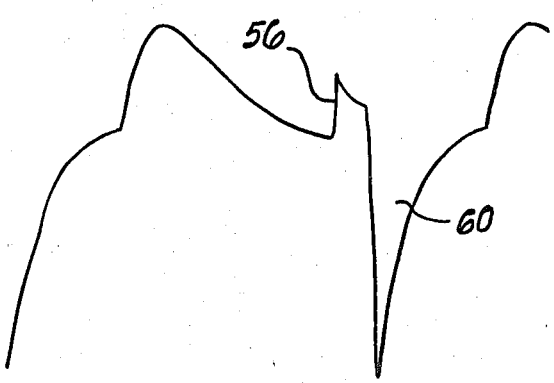

A further illustration is shown in FIGS. 21 and 22, which are two electrograms taken on the same patient one after the other, each showing an x trace, with the time scale compressed over that used in FIG. 20. The trace in FIG. 21 was obtained with a catheter using the stimulating electrode for the sensing also, a conventional approach.

FIG. 21 shows a stimulus 56 and the resulting sensed wave form 60. In fact, in this case, ventricular stimulation had resulted in a response. The trace in FIG. 22 was made with this same standard catheter. Sensed QRS complexes are indicated by 57. At 56, a stimulus is applied to the ventricle at a time when it can not respond—i.e is refractory. Note that wave form 60 is identical whether or not a ventricular response has occurred. Thus standard catheters are incapable of judging whether stimuli have resulted in responses.

In contrast, as shown in FIG. 20, using orthogonal ventricular sensing electrodes independent from the stimulating means, stimulus 56 clearly results in response 57 during complex 58, but there is no response to stimulus 56 in complex 59. In contrast with the configuration of FIG. 21 and 22, the pacing system as shown in FIG. 20 can determine whether or not there is heart response to the stimulus, even though it occurs within milliseconds of the stimulus.

In operation at specified times the pacemaker would decrease the current output at the distal pacing electrode and judge whether or not a response occurred as sensed by the sensing electrodes 20-24. When a response was not sensed, the pacemaker would recognize the lack of a QRS complex and simply double the stimulation threshold to the stimulation electrode 20. This would allow for maximum pacemaker battery longevity since stimulation threshold may be a constantly changing measurement. If desired the input from the sensing electrodes can be blanked at the time of the stimulation pulse. However even without this addition, QRS complexes are readily distinguished from stimulus artifacts.

Figure 23:
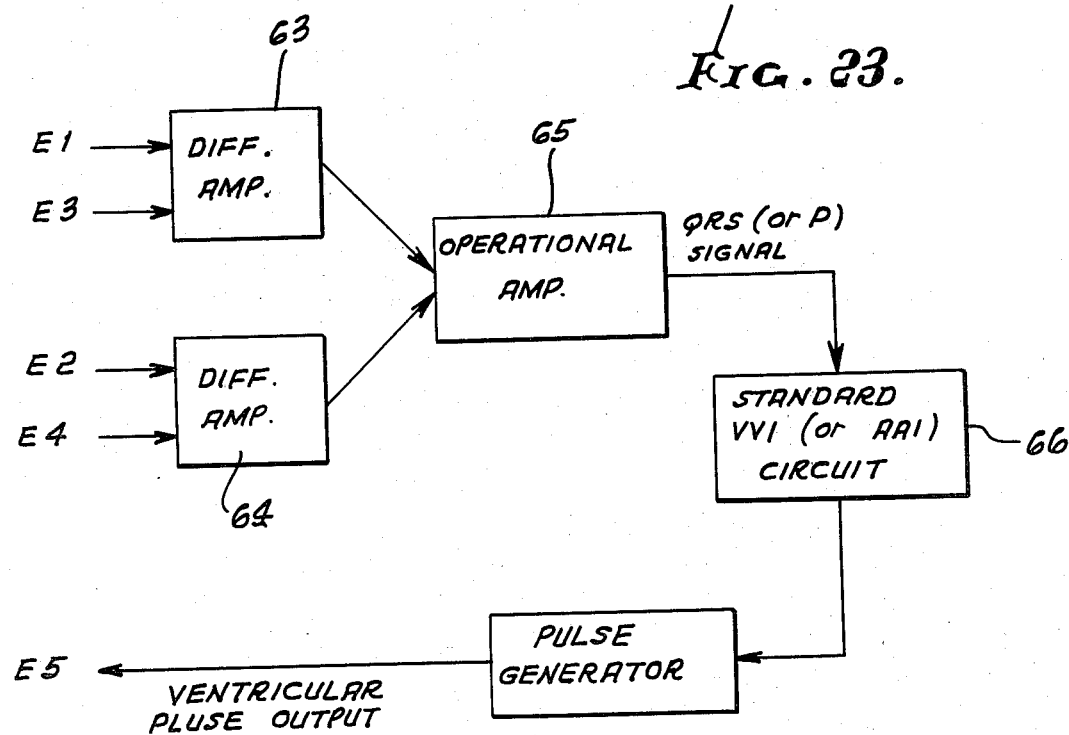
FIG. 23 is an electrical block diagram illustrating circuitry for VVI and AAI pacing.

A typical circuit for a VVI pacemaker is shown in FIG. 23, which is similar to that shown in FIG. 4. Leads E1 and E3 are connected as inputs to a differential amplifier 63, and leads E2 and E4 are connected as inputs to another differential amplifier 64. The amplifier outputs are connected to an operational amplifier 65 which may perform summing or more complex manipulations on the signals as desired. The output of the operational amplifier is the desired QRS signal, which is provided as an input to a standard VVI circuit 66. Of course, if desired, only a single differential amplifier may be used, and the operational amplifier may be omitted. The output from the VVL circuit 66 is connected as an input to a pulse generator 67 which provides the stimulus pulse to electrode E5. The standard VVI circuit provides for blocking sensing for about 300 milliseconds after the stimulus pulse, which is a necessary delay because the QRS complex signal is not discriminated from other voltages with the conventional catheter. After the delay, the standard circuit looks for heart action and if it is sensed, the timing circuit is reset. if it is not sensed, a stimulus pulse is provided. When using the catheter of the present application, the delay can be reduced from 300 milliseconds to 10 milliseconds, permitting sensing immediately following the stimulus.

Another advantage of the present invention is that by sensing whether or not the stimulus evokes a response immediately, the pacing system can be utilized to correct an abnormal heart rhythm. Ventricular tachycardia is a condition wherein the heart beats at a very high rate and usually is corrected by applying one or more stimulating pulses to the heart to break up the rhythm of the high rate. In the past, the high rate heart action has been sensed and a stimulating pulse has been provided. However, the pacing system has not been able to measure the result of the stimulatng pulse. The catheter utilized with the VVI configuration of the present invention can be utilized with a tachy converting pacemaker to sense heart response to a stimulus even during tachycardia and indicate whether or not the stimulus has evoked a response.

The catheter of the invention also may be used for sensing P waves at the atrial level in patients with intermittent sinus node dysfunction. In these patients whose AV conduction is normal, the problem has to do with intermittent failure of the dominant pacemaker of the heart to fire. Whereas they have a normal response to rates at the atrial level, intermittently the sinus node fails to result in atrial depolarization, and the rate abruptly falls. With the bipolar and orthogonal sensing system of the invention positioned in the atrium, the electronics can be designed so that when P waves fail to occur at a predetermined rate, the atrium itself could be stimulated. This would be termed an AAI pacemaker, that is atrial sensing and atrial stimulating or inhibited pacemaker. Such a pacemaker would have some definite therapeutic advantages over the typical VVI pacemaker currently used for intermittent sinus node dysfunction.

Figure 14:
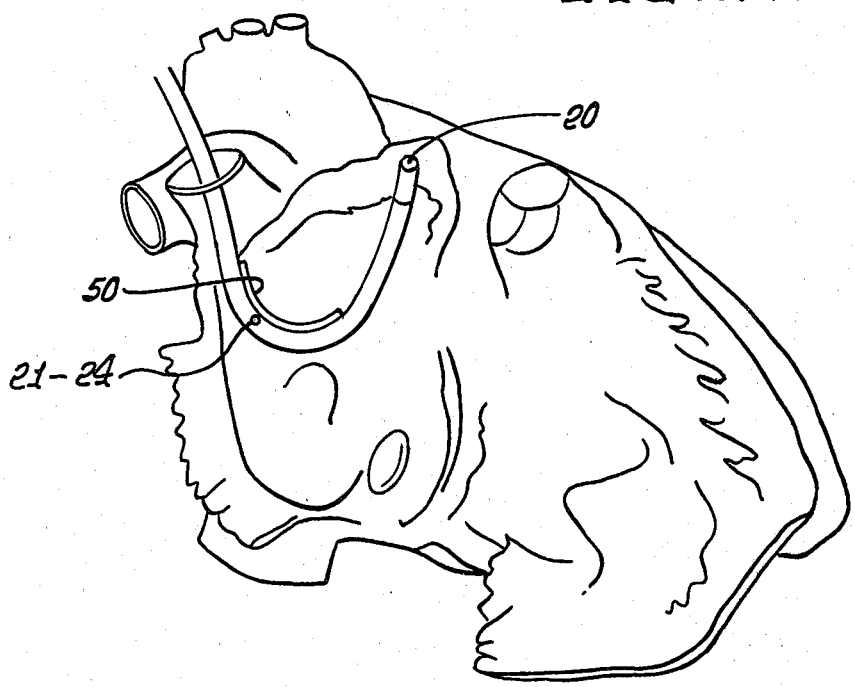

A modification of the standard J-shaped atrial pacing electrode to incorporate the present invention for AAI pacing is illustrated in FIG. 14. There is a ridge 50 in this electrode which causes it to retain its J configuration. The pacing electrode 20 is lodged within the right atrial appendage. The sensing electrodes 21 through 24 are in the high lateral right atrium quite separate from the distal pacing electrode. This type of pacemaker would be utilized with patients having intermittent sinus node dysfunction. At times when their atrial rate exceeded the predetermined rate of the pacemaker, signals sensed by electrodes 21 through 24 would inhibit any output through the pacing circuit. Were the rate of the normal sinus node pacemaker to drop below the predetermined level of the electronic pacemaker then stimuli would be applied to the right atrial appendage at a rate predetermined by the electronic pacemaker. This rate might be simply a fixed number, e.g. 75, or might be a function of the previous sinus rate such that where the heart rate precedent to the loss of P wave was 80, the atria would be paced at this rate until such time as the sinus node again exceeded the rate of the pacemaker itself. As can be seen in the heart diagram, the right atrial appendage overlies the pulmonary outflow tract. Thus signals sensed at the conventional tip electrode frequently reflect as large a QRS complex as they do a P wave. An electrogram for this condition would be essentially the same as that of FIG. 16. With independent sensing electrodes in the atrium, a reliable source of P wave sensing is available and many problems thus far encountered with this type of pacemaker would be obviated. A circuit for AAI pacing may be the same as that of FIG. 23, except that a standard AAI circuit is used in place of the standard VVI circuit 66, and that the sensed signal is a P wave signal rather than a QRS signal.

Figure 15:
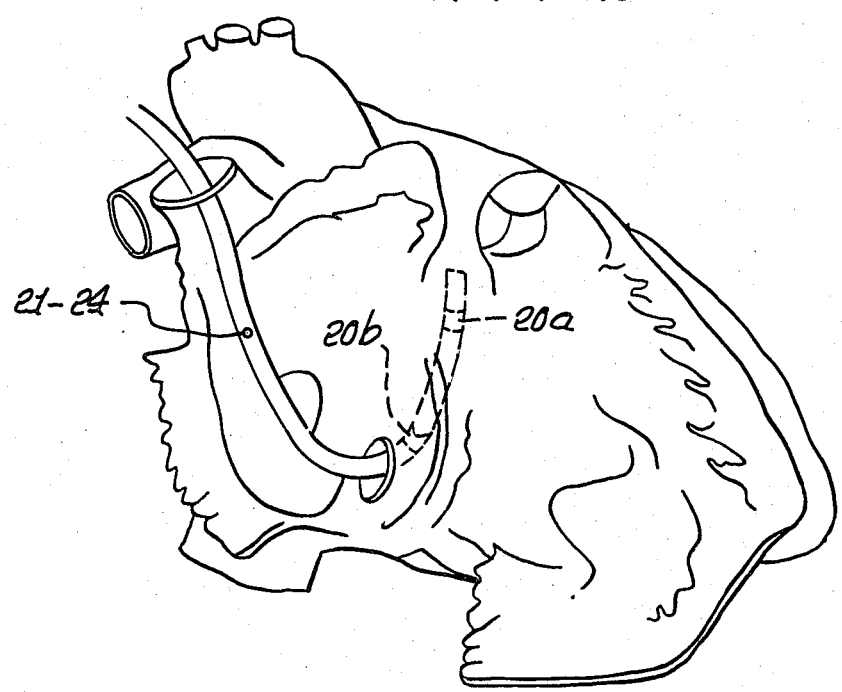

The configuration illustrated in FIG. 15 is a modification of the previous atrial sensing atrial pacing pacemaker of FIG. 14 in that the stimulating electrode is located either one centimeter back from the tip within the coronary sinus 20a or three or four centimeters back just at the origin of the coronary sinus 20b. Again the sensing electrodes in this atrial sensing atrial pacing catheter would be located in the high lateral right atrium. The problem with currently existing coronary sinus pacemakers is that the QRS complex is of equal or greater amplitude than the P wave as sensed from electrodes either one centimeter of four centimeters back from the tip of a catheter located in the coronary sinus. Thus, adequate sensing of P waves has been impossible. With the sensing electrodes 20-24 located circumferentially around the catheter in the high lateral right atrium, this problem would be obviated. The configuration of FIG. 15 may be operated in the same manner as that of FIG. 14.

I claim:

1. An electrode system for a cardiac pacer comprising a catheter in the form of a single nondiverging filament for insertion into a heart through the vascular system and including in combination:
   first stimulating electrode means at the distal end of said catheter for positioning the apex of the right ventricle;
   second sensing electrode means on said catheter and spaced from said stimulating electrode means for positioning adjacent the wall of the heart atrium and producing signals varying as a function of the cardiac P wave and including at least first and second electrodes mounted in the wall of said catheter equidistant from said distal end and insulated from each other and providing a bipolar signal to said cardiac pacer; and
   electrical conductor means for connecting said sensing electrode means to a cardiac pacer providing said signals as input and for connecting the output of a pulse generating unit of the cardiac pacer to said stimulating electrode means.

2. A device as defined in claim 1 wherein said sensing electrode means includes first, second, third and fourth electrodes mounted in the wall of said catheter equidistant from said distal end and substantially equally spaced from each other, with said first and third electrodes disposed opposite each other forming a first set and with said second and fourth electrodes disposed opposite each other forming a second set, with the first and second sets sensing orthogonal components of the cardiac P wave.

3. A device as defined in claim 2 wherein said sensing electrode means is spaced from said stimulating electrode means a distance corresponding to the distance between the apex of the right ventricle and the high lateral wall of the right atrium.

4. A device as defined in claim 2 wherein said sensing electrode means is spaced from said stimulating electrode means in the order of 10 to 18 centimeters.

5. In a cardiac pacer the improvement including in combination:
   a catheter in the form of a single nondiverging filament for insertion into a heart through the vascular system;
   first stimulating electrode means at the distal end of said catheter for positioning in the apex of a heart ventricle;
   second sensing electrode means on said catheter and spaced from said stimulating electrode means for positioning adjacent the wall of the heart atrium and producing signals varying as a function of the cardiac P wave and including at least first and second electrodes mounted in the wall of said catheter equidistant from said distal end and circumferentially positioned around the catheter and insulated from each other and providing a bipolar signal;
   means for generating a stimulating pulse in response to an input signal;
   means for connecting said stimulating pulse to said first stimulating electrode means; and
   means for connecting said bipolar signal as an input signal to said generating means.

6. A cardiac pacer as defined in claim 5 wherein said sensing electrode means includes first, second, third and fourth electrodes mounted in the wall of said catheter equidistant from said distal end and substantially equally spaced from each other and positioned circumferentially about said catheter with said first and third electrodes disposed opposite each other forming a first set and with said second and fourth electrodes disposed opposite each other forming a second set, with the first and second sets sensing orthogonal components of the cardiac P wave; and said means for generating includes:
   a first differential amplifier having said first electrode set connected as input and a second differential amplifier having said second electrode set connected as input; and
   a logic unit having the output of said first and second amplifiers as inputs and providing the larger of the input signals as output for said generating means.

7. In a cardiac pacer having means for receiving a P wave signal as an input and providing a stimulating pulse for a stimulating electrode as an output, the improvement including in combination:
   a single catheter in the form of a single nondiverging filament for insertion into a heart through the vascular system;
   first stimulating electrode means at the distal end of said catheter for positioning in the apex of a heart ventricle;
   second sensing electrode means on said catheter and spaced from said stimulating electrode means for positioning adjacent the wall of the heart atrium and producing signals varying as a function of the cardiac P wave and including first and second pairs of electrodes mounted in the wall of said catheter equidistant from said distal end and circumferentially positioned about said catheter with the electrodes of said first pair forming a first set and with the electrodes of said second pair forming a second set, with the first and second sets sensing orthogonal components of the cardiac P wave and providing bipolar signals; and
   circuit means having said bipolar signals as inputs for providing a P wave signal as an output varying as a function of the combination of said bipolar signals.

8. A device as defined in claim 7 wherein said circuit means includes a first differential amplifier having one of said bipolar signals as input;
a first band pass filter having the output of said first differential amplifier as input;
a second differential amplifier having the other of said bipolar signals as input;
a second band pass filter having the output of said second differential amplifier as input; and
means for combining the outputs of said first and second filters to provide the P wave signal.

9. A device as defined in claim 8 wherein said means for combining includes an operational amplifier.

10. A process for stimulating the heart action as a function of body requirements, including the steps of:
sensing a cardiac P wave at a pair of electrodes closely adjacent each other in a catheter in the form of a single nondiverging filament, with the electrodes located adjacent the atrium wall equidistant and spaced from a stimulation electrode and producing a bipolar electrical signal varying as a function of the sensed P wave;
generating electrical pulses and varying the pulse rate as a function of said electrical signal; and
introducing said pulses into the ventricle of the heart by the stimulation electrode.

11. The process as defined in claim 10 including performing the sensing of the P wave at a location adjacent the high lateral wall.

12. The process as defined in claim 10 wherein said sensing step is carried out by sensing two orthogonal components of the P wave equidistant from the stimulation electrode.

13. The process as defined in claim 12 including selecting the larger of the sensed components for controlling the pulse rate.

14. The process as defined in claim 12 including combining the sensed components for controlling the pulse rate.

15. The process as defined in claim 12 including:
removing the QRS complexes from each of the orthogonal components providing filtered components; and
combining the filtered components into a single P wave signal.

16. The process as defined in claim 15 wherein said combining step comprises determining the area of the loop of the filtered orthogonal components.

17. The process as defined in claim 15 including:
determining the deviation of occurrence of the P wave signal from prior P wave signals; and
when such deviation exceeds a predetermined value, producing said electrical signal for generating said electrical pulses.

18. The process as defined in claim 17 wherein said deviation is determined by:
determining the intervals between a sequence of P wave signals;
averaging such intervals to obtain an average interval; and
comparing the most recent interval with the average interval.

19. An electrode system for a cardiac pacer comprising a catheter in the form of a single nondiverging filament for inserting into a heart through the vascular system and including in combination;
first stimulating electrode means adjacent the distal end of said catheter for positioning within the heart;
second sensing electrode means on said catheter and spaced from said distal end for positioning within and adjacent the wall of the heart and producing signals varying as a function of cardiac electrical output and including at least first and second electrodes mounted in the wall of said catheter equidistant from said distal end and insulated from each other and providing a bipolar signal to said cardiac pacer; and
electrical conductor means for connecting said sensing electrode means to a cardiac pacer providing said signals as input and for connecting the output of a pulse generating unit of the cardiac pacer to said stimulating electrode means.

20. A device as defined in claim 19 wherein said sensing electrode means includes first and second pairs of electrodes mounted in the wall of said catheter equidistant from said distal end, with the electrodes of said first pair spaced from each other forming a first set and with the electrodes of said second pair spaced from each other forming a second set, with the first and second sets sensing orthogonal components of cardiac electrical output.

21. A device as defined in claim 20 wherein said first pair comprises first and second electrodes and said second pair comprises third and fourth electrodes.

22. A device as defined in claim 20 wherein said first pair comprises first and second electrodes and said second pair comprises said first electrode and a third electrode.

23. In a cardiac pacer the improvement including in combination:
a catheter in the form of a single nondiverging filament for inserting into a heart through the vascular system;
first stimulating electrode means adjacent the distal end of said catheter for positioning within the heart;
second sensing electrode means on said catheter and spaced from said distal end for positioning within and adjacent the wall of the heart and producing signals varying as a function of cardiac electrical output, and including first and second pairs of electrodes mounted in the wall of said catheter equidistant from said distal end, with the electrodes of said first pair forming a first set and with the electrodes of said second pair forming a second set, with the first and second sets sensing orthogonal components of cardiac electrical output and providing two bipolar signals; and
circuit means having said bipolar signals as inputs for providing a heart function signal as an output varying as a function of the combination of said bipolar signals.

24. A device as defined in claim 23 wherein said circuit means includes a first differential amplifier having one of said bipolar signals as input;
a first band pass filter having the output of said first differential amplifier as input;
a second differential amplifier having the other of said bipolar signals as input;
a second band pass filter having the output of said second differential amplifier as input; and
means for combining the outputs of said first and second filters to provide the heart function signal.

25. A device as defined in claim 24 wherein said means for combining includes an operational amplifier.

26. A process for stimulating the heart action as a function of body requirements, including the steps of:
sensing a cardiac electrical output at a pair of electrodes closely adjacent each other in a catheter in the form of a single nondiverging filament, with the electrodes located within and adjacent the wall of the heart and equidistant and spaced from a stimulation electrode in the catheter and producing a bipolar electrical signal varying as a function of the sensed heart electrical output;
generating electrical pulses and varying the pulse rate as a function of said electrical signal; and
introducing said pulses into the heart by the stimulation electrode.

27. The process as defined in claim 26 including sensing two orthogonal components of the cardiac electrical output equidistant from the stimulation electrode.

28. The process as defined in claim 27 including selecting the larger of the sensed components for controlling the pulse rate.

29. The process as defined in claim 27 including combining the sensed components for controlling the pulse rate.

30. A process for stimulating the heart action as a function of body requirements, including the steps of:
at predetermined time intervals sensing a cardiac QRS complex at a pair of electrodes closely adjacent each other in a catheter in the form of a single nondiverging filament, with the electrodes located in the heart adjacent the ventricle wall and equidistant and spaced from a stimulation electrode and producing a bipolar electrical signal indicating occurrence of the sensed QRS complex;
in the absence of the electrical signal at the predetermined time intervals generating an electrical pulse; and
introducing said pulse into the ventricle of the heart by the stimulation electrode.

31. The process as defined in claim 30 including; periodically generating the electrical pulses;
reducing the current amplitude of the pulses; and
in the absence of the electrical signal at a predetermined time interval, increasing the current amplitude of the pulses.

32. The process as defined in claim 30 including sensing two orthogonal components of the QRS complex equidistant from the stimulation electrode.

33. The process as defined in claim 32 including selecting the larger of the sensed components.

34. The process as defined in claim 32 including combining the sensed components.

35. A process for stimulating the heart action as a function of body requirements, including the steps of:
sensing a cardiac P wave at a pair of electrodes closely adjacent each other in a catheter in the form of a single nondiverging filament, with the electrodes located in the high lateral right atrium equidistant and spaced from a stimulation electrode in the catheter and producing a bipolar electrical signal indicating occurrence of the sensed P wave;
generating electrical pulses;
inhibiting an electrical pulse when a P wave has been sensed:
introducing said pulses into the right atrial appendage of the heart by the stimulation electrode.

36. The process as defined in claim 35 including sensing two orthogonal components of the P wave equidistant from the stimulation electrode.

37. The process as defined in claim 36 including selecting the larger of the sensed components for controlling the stimulation pulse.

38. The process as defined in claim 36 including combining the sensed components for controlling the stimulation pulse.

39. A process for stimulating the heart action as a function of body requirements, including the steps of:
sensing a cardiac P wave at a pair of electrodes closely adjacent each other in a catheter in the form of a single nondiverging filament, with the electrodes located in the high lateral right atrium equidistant and spaced from a stimulation electrode in the catheter and producing a bipolar electrical signal indicating an occurrence of the sensed P wave;
generating electrical pulses;
inhibiting an electrical pulse when a P wave has been sensed: and
introducing said pulses into the heart at the coronary sinus by the stimulation electrode.

40. The process as defined in claim 39 including sensing two orthogonal components of the P wave equidistant from the stimulation electrode.

41. The process as defined in claim 40 including selecting the larger of the sensed components for controlling the pulse rate.

42. The process as defined in claim 40 including combining the sensed components for controlling the pulse rate.

* * * * *